United States Patent [19]

Sacks et al.

[11] Patent Number: 4,937,330
[45] Date of Patent: Jun. 26, 1990

[54] CONVERSION OF CEPHALOSPORIN HYDROHALIDE SALT TO ALKALI METAL SALT

[75] Inventors: Clifford E. Sacks, Portage; Loren H. Dill, Kalamazoo, both of Mich.

[73] Assignee: The Upjohn Company, Kalamazoo, Mich.

[21] Appl. No.: 38,791

[22] PCT Filed: Jul. 31, 1986

[86] PCT No.: PCT/US86/01635

§ 371 Date: Apr. 10, 1987

§ 102(e) Date: Apr. 10, 1987

[87] PCT Pub. No.: WO87/01117

PCT Pub. Date: Feb. 26, 1987

Related U.S. Application Data

[63] Continuation of Ser. No. 764,877, Aug. 12, 1985, abandoned.

[51] Int. Cl.$^5$ ............... C07D 501/36; A61K 31/545
[52] U.S. Cl. ........................... 540/227; 540/226; 540/222
[58] Field of Search ............ 540/227, 226, 222, 230

[56] References Cited

U.S. PATENT DOCUMENTS

| | | | |
|---|---|---|---|
| 3,840,535 | 10/1974 | Kaplan et al. | 260/243 C |
| 4,224,371 | 9/1980 | Amiard et al. | 424/246 |
| 4,289,695 | 9/1981 | Chon | 260/239 A |
| 4,464,367 | 8/1984 | Labeeuw et al. | 424/246 |
| 4,478,749 | 10/1984 | Koster et al. | 260/245.4 |
| 4,717,768 | 1/1988 | Robinson et al. | 540/225 |

FOREIGN PATENT DOCUMENTS 0036812  9/1981  European Pat. Off. .
85307417.7  5/1986  European Pat. Off. .

OTHER PUBLICATIONS

Brochure: "Pyridine Functionality in Polymer Form", Reilly Tar & Chemical Corp., Indianapolis, Ind.
Chemistry and Biology of β-Lactam Antibiotics, vol. 3, Eds R. B. Morin, M. Gorman, Acad, Press, New York (1982).* *Title page and Contents only.

Primary Examiner—Nicholas S. Rizzo
Attorney, Agent, or Firm—Martha A. Cox

[57] ABSTRACT

The present invention relates to processes for the preparation of alkali metal salts of amino acids. Preferably, the present invention relates to solid phase alkali metal salts of cephalosporins of formula III, wherein M is selected from the group consisting of sodium, potassium and lithium, characterized by birefringent lath- and rod-shaped particles, and processes for their manufacture.

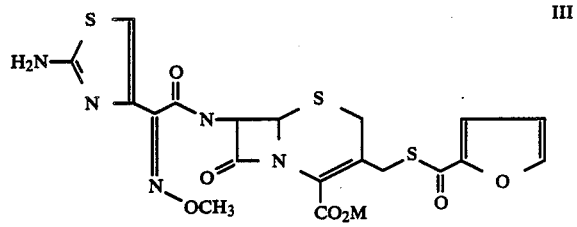

6 Claims, No Drawings

CONVERSION OF CEPHALOSPORIN HYDROHALIDE SALT TO ALKALI METAL SALT

This is a continuation of Ser. No. 764,877, filed 8/12/85, now abandoned.

BACKGROUND OF THE INVENTION

1. Field of Invention

The present invention relates to a novel process for preparing the alkali metal salts of an amino acid from the corresponding mineral acid salts. More specifically, the present invention relates to novel solid phase alkali metal salts of a cephalosporin antibiotic and to a process for preparing the cephalosporin alkali metal salts substantially free of impurities, from the corresponding hydrohalide salts

2. Information Disclosure

The cephalosporin antibiotic 7-[2-(2-amino-1,3-thiazol-4-yl)-2-methoxyimino)acetamido]-3-[(fur-2-ylcarbonyl)thiomethyl]-3-cephem-4-carboxylic acid (also named 7-[2-(2-amino-4-thiazolyl-2-methoxyimino)-acetamido]-3-[2-(furanylcarbonylthiomethyl)-8-oxo-5-thia-1-azabicyclo-[4,2,0]oct-2-ene-1-carboxylic acid) of formula I, its alkali metal, alkaline earth metal and amine salts of the carboxylic acid group, and easily hydrolyzable ester groups thereof are described and claimed in Labeeuw et al., U.S. Pat. No. 4.464.367. This cephalosporin free acid compound of formula I is now known by the generic name ceftiofur.

These patented free acid and cationic metal and amine salt and ester forms of this cephalosporin antibiotic are somewhat unstable chemically and are obtained as amorphous compounds which are difficult to purify, and are less desirable to work with in manufacturing pharmacuetical formulations containing them.

Methods for the conversion of cephalosporin acids to their corresponding sodium salts are known. U.S. Pat. No. 4,224,371 describes the preparation and crystallization of the crystalline sodium salt from mixing cefotaxime and sodium acetate in aqueous alcohols. U.S. Pat. No. 3,840,535 discloses the use of sodium 2-ethylhexanoate to prepare the sodium salt of cephalosporins.

Crystalline hydrohalide salts of ceftiofur are described in European Patent Application 85307417.7, published May 7, 1986 (Publication Number 0180372).

The use of polyvinylpyridine as a hydrogen chloride scavenger during cephalosporin ring cleavage reactions is described in U.S. Pat. No. 4,289,695 (1981).

A brochure, entitled "Pyridine Functionality in Polymer Form," published by Reilly Tar and Chemical Corporation, Indianapolis, IN, describes the use of derivatives of polyvinylpyridine as acid scavengers.

SUMMARY OF INVENTION

The present invention relates to a process for preparing the alkali metal salts of an amino acid from the corresponding mineral acid salts. The preferred process of this invention is to prepare the alkali metal salts of a cephalosporin antibiotic from the corresponding hydrohalide salts.

The present invention particularly provides:

A solid phase cephalosporin compound of formula III wherein M is selected from the group consisting of sodium, potassium and lithium, characterized by birefringement lath- and rod-shaped particles;

a process for preparing an alkali metal salt of an amino acid, which comprises:

(a) neutralizing a mineral acid salt of the amino acid in an aqueous organic solvent by treating it with a basic resin;

(b) filtering the solution prepared in step (a) to remove the basic resin;

(c) treating the filtrate obtained in step (b) with a base of an alkali earth metal; and a method for neutralizing a cephalosporin or penicillin acid salt, which comprises treating the salt with polyvinylpyridine.

The term "amino acid" as used in the process of this invention refers to a compound of formula $NH_2$-R-COOH wherein R is an aliphatic radical, derivative thereof, or a more complex radical such as those contained in cephalosporins and penicillins. Therefore, naturally, occurring as well as synthetic amino acids are included within this definition. Such compounds are well known and readily available to those skilled in the art, for example, cephalosporin, penicillin, alanine, glycine, and α-phenylglycine.

The term "cephalosporin" as used in this invention is a bicyclic, monocarboxylic acid isolated from strains of Cephalosporium or derivatives thereof and useful as an antibiotic. The term "cephalosporin" as used in this invention is understood to include its tautomers as well as the mixture of the cephalosporin and its tautomers. Cephalosporins preferred for use in this invention include those having an amino group in the moiety attached to the 7-position of the cephalosporin nucleus and especially those capable of forming hydrohalide salts. U.S. Pat. No. 4,478,749, which is hereby incorporated by reference, provides a detailed description of the groups used to acylate the 7-position of 7-aminocephalosporanic acid and its derivatives. "Chemistry and Biology of β-Lactam Antibiotics," Vol. 3, R. B. Morin and M. Gorham, ed., Academic Press, N.Y., 1982, which is also hereby incorporated by reference, provides a list of groups which are preferred for acylating the 7-position of 7-aminocephalosporanic acid and its derivatives. Examples of cephalosporins useful in the process of this invention include the Cefotaxime and Ceftiofur cephalosporins.

The process of converting the cephalosporin hydrohalide salt to its alkali metal salt poses many difficulties. If the hydrohalide salt were treated directly with base, e.g., sodium ethylhexanoate, the isolated sodium salt would likely contain unacceptably high levels of sodium chloride. Alternatively, one could neutralize the cephalosporin hydrohalide salt, isolate the neutralized salt, wash it to remove inorganic salts (e.g., sodium chloride), convert it to its sodium salt, and then isolate the sodium salt. However, removal of the inorganic salts by isolation and washing is tedious due to the poor filtration characteristics of the muddy cake. Additionally, workers must be exposed to dusty solids when the isolated cake is transferred to a reaction vessel for subsequent processing, thereby creating a potential health hazard.

The conversion of the cephalosporin hydrohalide salt to its alkali earth metal salt, according to the process of this invention, overcomes many of these problems. According to the novel process of this invention, the use of a basic resin. e.g., polyinylpyridine, obviates the necessity to isolate the intermediate neutralized salt and reduces the risk of cephalosporin exposure to workers. Treatment of the hydrohalide salt with polyvinylpyridine and filtration produces a solution of the cephalosporin which is substantially free of inorganic salts.

Subsequent direct treatment of the cephalosporin solution with base (e.g. sodium bicarbonate, sodium methoxide, sodium acetate or sodium 2-ethylhexanoate,) produces the desired sodium salt. Use of a potassium or lithium base produces the corresponding alkali salt.

Any ion-exchange resin with basic residues may be used in the process of this invention. More preferred are ion-exchange resins with weakly basic residues, e.g., Dowex MWA-1, Duolite C-464 and Duolite A-340, C-433.

The use of polyvinylpyridine as the basic resin in the process of this invention is most preferred. Polyvinylpyridine has several properties which makes it preferred over other basic resins: stability to osmotic shock, easily recyclable, high loading capacity and almost total lack of affinity for the cephalosporin. According to the process of this invention, polyvinylpyridine can effectively be used to neutralize the mineral acid salt (e.g., sulfuric acid, phosphoric acid, perchloric acid) of any amino acid and to produce, after filtration, a solution substantially free of inorganic salts.

The use of sodium 2-ethylhexanoate as a base for the sodium salt formation, according to the process of this invention, is preferred. Sodium ethylhexanoate has the advantage over sodium acetate because it is soluble in organic solvents and an excess of reagent can be used.

The resulting alkali metal salt may be isolated by an appropriate method (e.g., solvent removal or precipitation). The alkali salt which is isolated is substantially free of foreign inorganic salts.

In the process of this invention, certain solvent systems are preferred for certain cephalosporins for reasons of chemical stability, solubility, isolation characteristics, and/or product purity. The use of aqueous tetrahydrofuran is preferred for the sodium salt of the cephalosporin ceftiofur. The superior precipitation, isolation, and purity of the sodium salt from aqueous tetrahydrofuran makes it the preferred solvent. Other organic solvents which have at least some capacity for water, e.g. acetone/water or ethyl acetate/water, may also be used.

The present invention also provides novel solid phase alkali metal salts of the ceftiofur cephalosporin. The ceftiofur sodium salt as isolated from aqueous tetrahydrofuran is a unique solid phase characterized by birefringent lath- and rod-shaped particles. When examined by x-ray diffraction, the particles, while having characteristic properties, such as refractive indices, which are $n \approx 1.624$ and $n \approx 1.660$, gave no diffraction pattern. The substantially improved precipitation and filtration characteristics observed for the ceftiofur sodium salt are attributed to the properties of this unique phase. Specifically, the occurrence of oiling of the product upon precipitation, which is common with other solvent systems, is reduced when aqueous tetrahydrofuran is used. Furthermore, the filtration cake is less compressible and filtration rates are above those experienced with other solvents.

The use of aqueous tetrahydrofuran to isolate the cephalosporin salt may occur in any one of several ways: (1) the alkali metal salt may be dissolved in aqueous tetrahydrofuran and then precipitated by the controlled addition of dry tetrahydrofuran; (2) the alkali metal salt solution can be added directly to the dry tetrahydrofuran in a controlled manner; or (3) an aqueous tetrahydrofuran solution of the cephalosporin may be added to a dry tetrahydrofuran solution of an appropriate base. In all cases, the quasi-crystalline alkali metal salt is formed in a readily isolable form.

Treatment of the sodium salt with a dry organic solvent (e.g., acetone or ethanol) produces solvent-free solids upon drying. The unique phase described above is destroyed by such treatment, and only amorphous particles exhibiting no birefringence remain. Other dry organic solvents include: isopropyl alcohol and ethyl acetate. Acetone is the most preferred solvent.

The preferred method of this invention for the conversion of ceftiofur cephalosporin hydrohalide salt to its alkali salt is to use polyvinylpyridine with aqueous tetrahydrofuran as solvent to produce a neutralized cephalosporin solution. The preferred method of this invention for the isolation of the alkali salt is to add the neutralized cephalosporin solution, after filtration, to a dry tetrahydrofuran solution of sodium 2-ethylhexanoate followed by filtration, washing with dry acetone, and drying at 20° to 25° C. with nitrogen. The resulting product is substantially free of inorganic by-products and solvents.

European Patent Application 85307417.7, published May 7, 1986 (Publication Number 0180372), which is incorporated by reference herein, discloses the process for making the ceftiofur cephalosporin hydrohalide salt used in the process of this invention. Preparation 1 below describes the best mode now known for the preparation of the 7-amino precursor 3-cephem-4-carboxylic acid nucleus compound.

The compounds of Formulae II and III herein are useful as the active antibiotic drug compounds in pharmaceutical dosage forms to treat bacterial infections in valuable mammalian animals.

DESCRIPTION OF THE PREFERRED EMBODIMENTS

The invention is further illustrated by the following detailed preparations and examples:

PREPARATION 1.
(3-THIOFUROYL-7-AMINOCEPHALOSPORANIC ACID)

Step A. (Sodium Thiofuroate)

60.0 g (0.250 mole, 1.39 eq) of sodium sulfide nonahydrate is dissolved in 508 ml of water. The solution is degassed by applying vacuum and releasing with nitrogen. The pH of the solution is adjusted to pH 10 by adding .85% phosphoric acid. 17 ml of ethyl acetate is added. 22.0 ml (density = 1.324 29.1 g, 0.223 mole, 1.24 eq) of furoyl chloride is added dropwise while maintaining the pH of the solution at pH 9.0 to 9.5 by adding 25% sodium hydroxide solution. The furoyl chloride is rinsed in with 3 ml of ethyl acetate. Total addition time is approximately 30 minutes and the final temperature is 28°-30° C. When the reaction is complete, the pH is adjusted to pH 5.0 by adding 85% phosphoric acid and vacuum is applied to remove residual hydrogen sulfide. After 10 minutes, the vacuum is released with nitrogen. When all of the hydrogen sulfide is removed, the solution is heated to 60° C. and the pH adjusted to 6.4 by adding a 25% sodium hydroxide solution.

Step B

To the sodium thiofuroate solution prepared in Step A. 49.0 g (0.180 mole, 1.00 eq) of pulverized or powdered 7-amino-cephalosporanic acid and 20 ml of ethyl acetate is added. The slurry is stirred at 65° C. for four hours while maintaining a pH of 6.4±0.2. The pH of the hot slurry is then adjusted to 5.0 by adding 85% phosphoric acid and filtered. The flask is rinsed with 100 ml of 65° C. water and the cake is washed three times with 100 ml of 60° C. water. The product is dried by rinsing three times with 100 ml of acetone, one time with 100 ml of heptane and pulling dry with nitrogen on the filter. Final drying at 30° C. under vacuum for 18 hours gives a very light-colored, powdery, dusty solid with the characteristics of a fine sand.

PREPARATION 2. (ACTIVATION OF POLYVINYLPYRIDINE (PVP))

PVP is slurried and washed with 1:3 concentrated aqueous hydrochloric acid. It is then rinsed with water and washed with excess 10% sodium hydroxide solution. It is rinsed well with water, and then tetrahydrofuran (THF). It is air dried and then dried in a rotary evaporator.

EXAMPLE 1

Step A. (Conversion of cephalosporin hydrohalide salt to free base)

20 g (0.0357 mol) of hydrochloride salt of cephalosporin and 6.0 g (0.048 eq) of PVP (see Preparation 2) are slurried in 200 ml of 7% aqueous THF for 30 min. at 25° C. Polyvinylpyridinium hydrochloride and residual PVP are removed by filtration. The solids are rinsed with three 30 ml portions of 3% aqueous THF. Retain filtrates (volume: about 300 ml) for next step.

Step B. (Conversion of free base to sodium salt)

In a separate vessel, 4.0 g (0.050 mol) of 50% sodium hydroxide solution and 7.47 g (0.0518 mol) of 2-ethylhexanoic acid are mixed in 20 ml of THF. The mixture is stirred for 30 min, then added to the stirred solution from step A.

Step C. (Precipitation of sodium salt)

The solution from step B is added slowly to 1200 ml of THF over 20 min at 25° C. The resulting solution is cooled to 5° C. and the salt isolated by filtration. The filter cake is washed with two 50 ml portions of acetone and then soaked for 30 min in acetone (50 ml). The solids are blown dry with nitrogen and finally dried in a vacuum oven at 40° C. The yield is 17.36 g.

Physical characteristics of the sodium salt are as follows:

The nuclear magnetic resonance (NMR) spectrum was performed on 100 mg sample of the cephalosporin sodium salt dissolved in 0.5 ml of $d_6$-DMSO. The spectrum was recorded at 90 MHz on an EM-390.

$^1$H-NMR ($d_6$-DMSO): 5.50, 4.83, 4.21, 1.65, 0.86, 2.49, 3.08, 7 03, 1.31, 4 21, and 4.83.

$^{13}$C-NMR ($d_6$-DMSO): 162.3, 109.2, 142.4, 149.0, 168.6, 58.0, 57.3, 62.9, 133.0, 116.1, 26.4, 32.35, 180.2, 149.8, 116.5, 112.8, 147.8. 164.7, and 61.8.

The solubility of the sodium salt in THF/water mixtures was examined. Weighed samples of cephalosporin were mixed with measured volumes of solvent and stirred for four hours at 25° C. Samples of the supernatant (filtered through a 0.45 μ filter) were diluted and analyzed by high performance liquid chromatography (HPLC).

Solubility (mg/ml): <0.50 (0% water), 0.52 (0.5%), 0.92 (1.0%), 4.2 (3.0%), 21 (5.0%), 49 (7.0%), and <100 (10.0%).

The sodium salt crystal, as prepared by the process of this invention and as isolated from aqueous tetrahydrofuran, is probably a two-dimensional crystal since it showed good birefringence under the polarized microscope but a diffused pattern via x-ray powder diffraction.

EXAMPLE 2

(Conversion of cephalosporin hydrohalide salt to its sodium salt)

Step A. To a suitably prepared, appropriately-sized reaction vessel, is added:
 8.62 kg hydrochloride salt of cephalosporin
 4.31 kg PVP (activated as in Preparation 2)
 72.8 kg THF
 4.31 l water
The resulting solution is stirred for four hours.

Step B. In a separate large reaction vessel, is combined:
 108 kg THF
 3.44 kg 2-ethylhexanoic acid
 1.84 kg 50% sodium hydroxide solution
The resulting solution is stirred for 15 min and the pH is checked. The solution is stirred again until the pH is neutral.

Step C. The solution from step A is transferred through line filters into the vessel containing the sodium-ethyl hexanoate. It is stirred for 15 min. The product is filtered and the solids washed with 68.1 kg of dry acetone. The filter cake is dried with nitrogen. The yield is 6.8 kg of cephalosporin sodium salt.

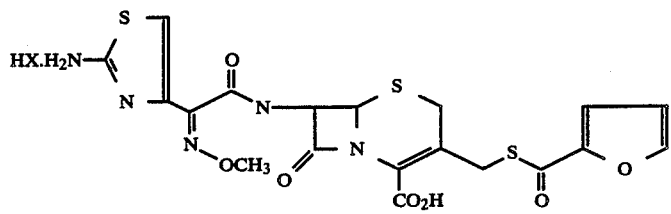

II

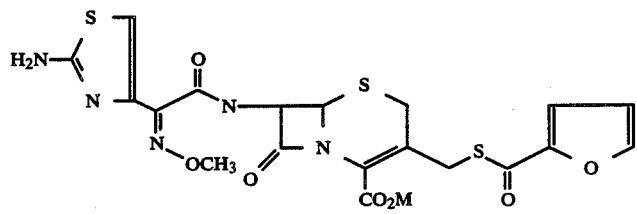

III

We claim:
1. A process for preparing a cephalosporin of formula III

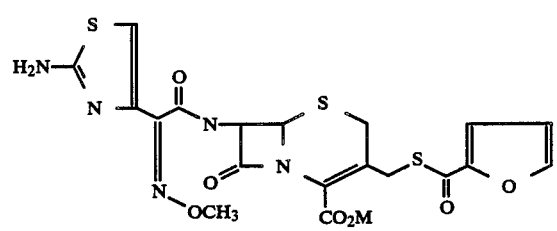

III wherein M is selected from the group consisting of sodium, potassium and lithium; which comprises:
(a) neutralizing a compound of formula II

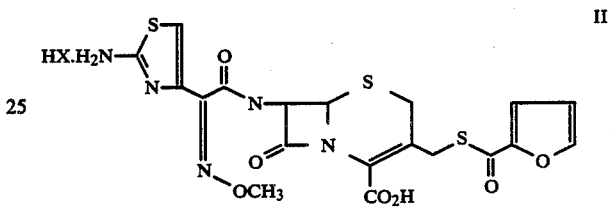

II wherein X is selected from the group consisting of chlorine and bromine;
in an aqueous organic solvent, by treating it with a basic resin;
(b) filtering the solution prepared in step (a) to remove the basic resin; and
(c) treating the filtrate obtained in step (b) with the base of an alkali earth metal.

2. A process according to claim 1 wherein the basic resin is polyvinylpyridine.

3. A process according to claim 2 wherein the aqueous organic solvent is aqueous tetrahydrofuran and the base is sodium-2-ethylhexanoate.

4. A process according to claim 1 which further comprises: step (d) isolating the compound of formula III by precipitation from an aqueous organic solvent.

5. A process according to claim 4 wherein the aqueous organic solvent is aqueous tetrahydrofuran.

6. A method of neutralizing a hydrohalide salt of a cephalosporin which comprises treating the salt with polyvinylpyridine.

* * * * *